US005769224A

United States Patent [19]
Poncy et al.

[11] Patent Number: 5,769,224
[45] Date of Patent: Jun. 23, 1998

[54] SHEATH PACKAGE FOR PIPETTERS

[76] Inventors: Richard Poncy, 120 Spinnaker La., Jupiter, Fla. 33477; George W. Poncy, Sr., 5380 N. Ocean Blvd., Apt. 12-J, Singer Island, Fla. 33404

[21] Appl. No.: 821,822

[22] Filed: Mar. 21, 1997

[51] Int. Cl.[6] .................................................. B65D 85/00
[52] U.S. Cl. ...................... 206/365; 206/306; 206/484.2; 206/569; 383/211; 422/100
[58] Field of Search .................................... 206/305, 306, 206/363–367, 484, 484.2, 569; 383/210, 211; 422/100

[56] References Cited

U.S. PATENT DOCUMENTS

| | | | |
|---|---|---|---|
| 3,732,975 | 5/1973 | Poncy | 206/306 |
| 3,809,230 | 5/1974 | Poncy | 206/484.2 |
| 4,142,631 | 3/1979 | Brandriff | 206/484.2 |
| 4,614,442 | 9/1986 | Poncy | 206/306 |
| 4,846,344 | 7/1989 | Bala | 206/306 |
| 5,069,337 | 12/1991 | Bala | 206/363 |
| 5,107,988 | 4/1992 | Bala | 206/306 |

*Primary Examiner*—Paul T. Sewell
*Assistant Examiner*—Luan K. Bui
*Attorney, Agent, or Firm*—Lane, Aitken & McCann

[57] ABSTRACT

A sterile packaging system for a pipetter sheath is disclosed. The packaging system comprises two inner thermoplastic strips sandwiched between two outer paper covers. The inner strips and outer covers are connected along a tear seal formed by an electromagnetic heat sealer. The tear seal is generally in the shape of a pipetter. To remove the sheath from the package and place it onto a pipetter, one of the outer covers is removed, the pipetter placed into the partially exposed sheath, and the remaining cover removed thereby leaving the sheath on the pipetter.

6 Claims, 4 Drawing Sheets

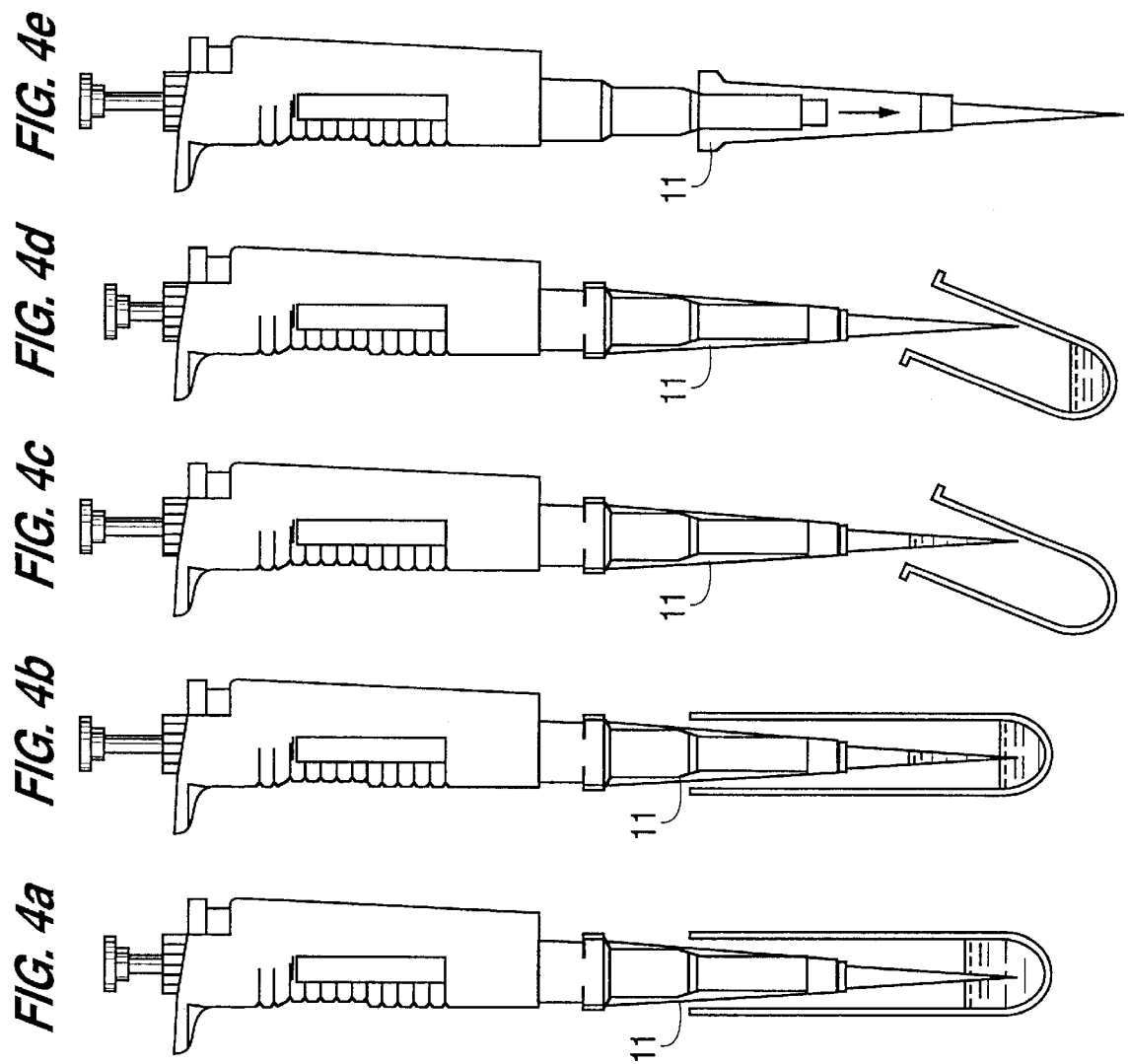

SHEATH PACKAGE FOR PIPETTERS

FIELD OF THE INVENTION

The present invention relates to a sterile package for a pipetter sheath.

BACKGROUND OF THE INVENTION

The use of a pipetter to transfer a medium or a portion thereof from one test tube or container to another is common in many industries and fields of research. In order to avoid contamination among the samples during the transfer by the pipetter, a plastic tip is placed on the end of the pipetter, the medium is drawn into the plastic tip, the medium is removed and placed into the target test tube, the plastic tip is discarded, and the process repeated for each transfer. The use of a separate sterilized plastic tip for each transfer prevents cross contamination between test tubes resulting from the plastic tip or any residue remaining in the plastic tip.

The use of sterilized plastic tips for each transfer of medium does not insure however that no test tube will become contaminated from the pipetter since the plastic tip is only about five or six centimeters in length thereby leaving the portion of the pipetter above the plastic tip exposed as a possible source of contamination. This contamination may occur if the portion of the pipetter above the plastic tip descends below the lip of the test tube and contaminates the inner walls of the test tube, which may in turn contaminate the medium in the test tube.

The potential for contamination can be reduced by placing a sterilized sheath over the pipetter which covers the upper portion of the plastic tip and the portion of the exposed pipetter above the plastic tip. In order for such a sheath to be practical however, a sterile packaging system which maintains the sterility of such a sheath is required.

SUMMARY OF THE INVENTION

Sheath packaging systems,for thermometers and other medical and surgical devices are disclosed in U.S. Pat. Nos. 3,552,558, 3,732,975, 3,809,230, 3,847,280 and 4,614,442. These patents also disclose methods of manufacture and use for these packaging systems.

The present invention comprises a sterile packaging system for a pipetter sheath. The sheath is used to cover the plastic tip and lower portion of a pipetter thereby preventing contamination of samples from which or into which medium is transferred using the pipetter. The sheath and the plastic tip are replaced after each sample is transferred to assure that a sterile tip and sheath are used for each transfer.

The sheath packaging system of the present invention comprises two inner strips of a flexible thermoplastic material, one which is greater in length than the other. These two strips of thermoplastic material are sandwiched between two paper cover strips, one which is referred to as a front cover strip and the other which is referred to as a back cover strip. Both the front and back cover strips have their inner surface coated with a thermoplastic material.

An electronic high frequency heat-sealing die is pressed onto the two paper strips and the two thermoplastic strips. High frequency current which runs through the die produces heat and along with the pressure of the die forms a tear seal between the two thermoplastic strips and a peelable seal between each paper cover strip and the thermoplastic strip in contact with it. The die has a tapered shape which generally corresponds to the shape of a pipetter with a tip end and a mouth end. The die forms the sheath by impressing the tear seal in the thermoplastic strips. Specifically, the die is U-shaped and the closed end of the die is placed beyond the end of the shorter thermoplastic strip near the tip end. The arrangement of the die extending beyond the end of the shorter thermoplastic strip leaves an opening through which the tip of the pipetter protrudes upon insertion of the pipetter.

The thermoplastic strips are laminated to both the front and back cover strips at both the mouth and tip ends of the sheath. The lamination at the tip end of the sheath allows the selvage portion, i.e. the portion of the thermoplastic strips which lies outside the bounds of the tear seal and which does not form part of the sheath, to remain attached to the front cover strip and to be removed therewith when the front cover strip is peeled away.

The longer thermoplastic strip at the tip end extends to the end of both the front and back cover strips. Both thermoplastic strips extend to the end of the front and back cover strips at the mouth end. To remove the sheath from the sterile packaging and place it onto the pipetter, the front cover strip and the longer thermoplastic strip extending to the end of it are grasped at the tip end and pulled back. This is referred to as a pre-peel, and since the front cover is pulled up past the tip end of the seal line, it prevents the pipetter tip from diving in between the selvage and the front cover when the pipetter is inserted therein. If the pipetter tip did penetrate between the selvage and the front cover, the pipetter tip would prevent the front cover and selvage from being pulled back.

When the front cover is peeled to the point where the seal line begins, the selvage portion of the longer thermoplastic strip tears away from the portion inside the seal line. Similarly, when the front cover reaches the point where the shorter thermoplastic strip begins, the selvage portion of the shorter thermoplastic also tears away from the portion of the thermoplastic strip which forms the sheath thereby leaving behind the sheath while the selvage is removed along with the front cover strip. The sheath is able to separate from the selvage because of the tear seal, and the front cover is able to separate from the sheath because of the peelable seal. After the removal of the front cover, the pipetter with attached plastic tip is inserted into the mouth end of the partially exposed sheath and pushed down beyond the opening for the tip. The back paper cover strip is then grasped at the tip end, pulled up, and removed from the sheath leaving the sheath on the pipetter. In the same manner as the front cover, the back cover separates from the sheath along the peelable seal.

Accordingly, it is an object of the invention to prevent the contamination of samples when transferring samples by pipetter.

It is another object of the invention to prevent such sample contamination by covering a pipetter with a thermoplastic sheath.

It is a further object of the invention to provide a sterile package in which to keep the thermoplastic sheath.

It is a still further object of the invention to allow the sheath to be easily separated from the package and placed onto the pipetter without damaging the sheath.

BRIEF DESCRIPTION OF THE DRAWINGS

FIGS. 4a–4e illustrate the manner in which a pipetter with a sheath placed thereon is used to transfer a sample from one test tube to another.

DETAILED DESCRIPTION OF THE PREFERRED EMBODIMENTS

Figure 1:
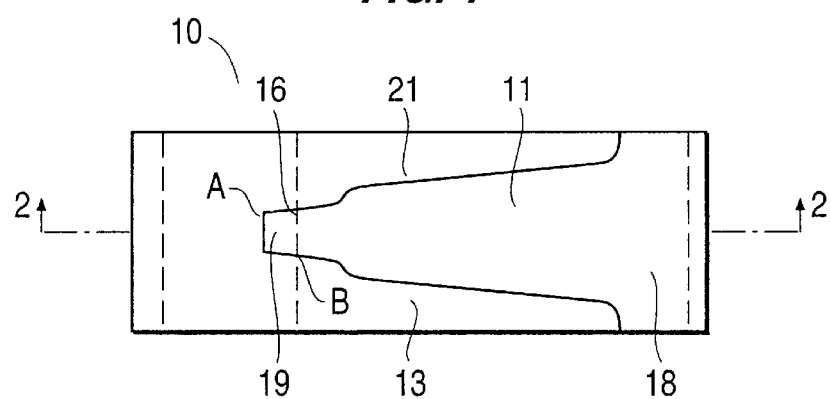
FIG. 1 is a plan view of the sheath package of the present invention.
Figure 2:
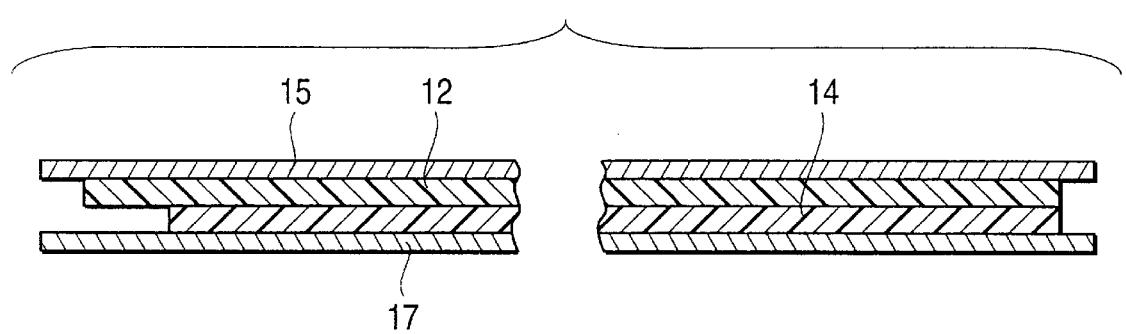
FIG. 2 is a cross section of the sheath package of FIG. 1 taken along line 2—2 in FIG. 1.

A plan view of the sheath package of the present invention is illustrated in FIG. 1, and a cross sectional view taken along line 2—2 of FIG. 1 is illustrated in FIG. 2. The thickness of the layers in FIG. 2 is exaggerated for clarity of illustration. The sheath package 10 encases pipetter sheath 11 which has a mouth portion 18 and a tip portion 19. Sheath package 10 comprises two inner strips 12 and 14 which are comprised of a flexible impervious thermoplastic material and are approximately 1 mil in thickness. The two inner strips 12 and 14 are covered by front cover strip 15 and back cover strip 17. The inside surfaces of the front and back cover strips 15 and 17 which come into contact with the inner strips 12 and 14 are coated with a flexible thermoplastic material which allows the inner strips 12 and 14 to be laminated to the front and back cover strips 15 and 17 respectively. This thin coating of the thermoplastic material on the outer strips 15 and 17 cannot be seen in either FIGS. 1 or 2 since the coating impregnates the paper.

The inner strips 12 and 14 and the front and back covers 15 and 17 are sealed together along seal line 21. Seal line 21 is formed by an electronic high frequency heat-sealing die whose use is well known in the industry. High frequency current which runs through the die produces heat and along with the pressure of the die forms a tear seal in the two thermoplastic strips (12 and 14). The tear seal formed in the two thermoplastic layers 12 and 14, being generally in the form of a pipetter tip which tapers from the wide mouth portion 18 to the tapered tip portion 19, forms the sheath 11. The heat and pressure from the die also forms a peelable seal between the front cover strip 15 and the thermoplastic strip 12 and the back cover strip 17 and the thermoplastic strip 14.

FIG. 2 is a cross section taken along line 2—2 of FIG. 1 and illustrates that inner thermoplastic strip 12 is longer than inner thermoplastic strip 14. Inner strip 12 is longer than inner strip 14 to allow the U-shaped die to form sheath 11 with an open end by placing the U-shaped portion of the die beyond the end of shorter strip 14. The die forms the tear seal in the portion of the package where the strips 12 and 14 coextend along the seal line 21 and forms a U-shaped tear line along the seal line 21 in the portion of the strip 12 extending beyond the strip 14. The U-shaped tear line in the portion of the strip 12 extending beyond the strip 14 connects to the ends of the tear seal at the end of the strip 14. An open ended die could not be used to form the sheath because there would be no continuous tear line along which the sheath 11 and the selvage 13 could separate. On the other hand, if both strips 12 and 14 extended beyond the die, the sheath 11 would have a closed end unsuitable for pipetter purposes.

Figure 3A:
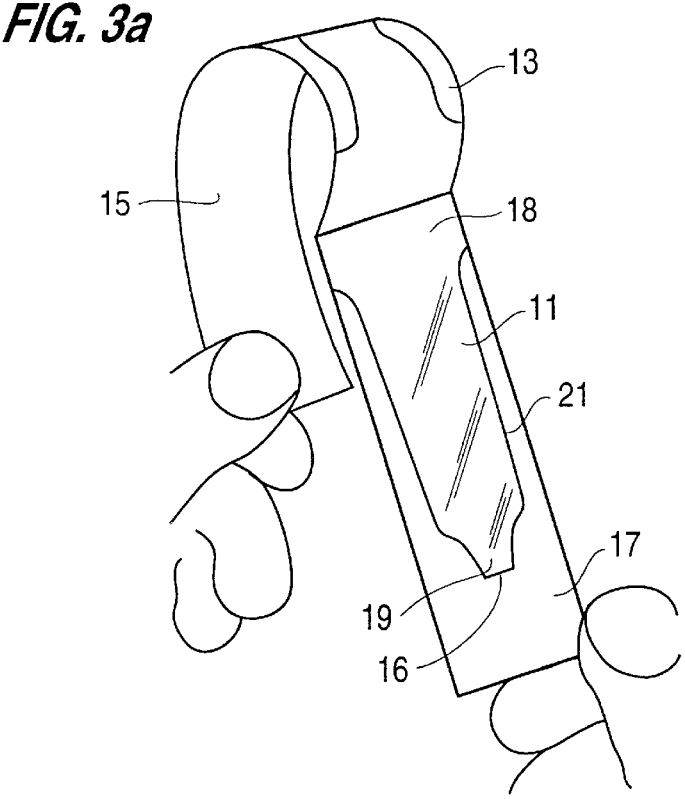
FIGS. 3a–3d illustrate the removal of the sheath from the sheath package and the placing of the sheath on the pipetter.

FIGS. 3a through 3d illustrate the manner in which the sheath 11 is placed onto a pipetter. FIG. 3a illustrates the manner in which the front cover 15 is grasped at the tip end 19 of the sterile package 10 and is peeled back off the back cover 17 exposing sheath 11. As front cover 15 is peeled back, the longer thermoplastic layer 12 is pulled along with the front cover 15 because the end of the thermoplastic layer 12 is laminated to the front cover 15. Upon the peeling reaching point A (FIG. 1), the tear line formed in the longer thermoplastic layer strip 12 causes the selvage of the strip 12 to separate from the thermoplastic portion inside the seal line 21, and the selvage portion 13 continues to be peeled back with the front cover 15. Removing the front cover 15 and the selvage 13 beyond point A prevents the pipetter tip from diving between the front cover 15 and the selvage 13 when the pipetter is placed into the sheath 11. As the front cover 15 and the thermoplastic strip 12 continue to be peeled back, the shorter thermoplastic strip 14 is exposed upon the peeling reaching point B. Upon the peeling reaching point B, the selvage portion of the shorter thermoplastic strip 14 begins to tear away from the sheath 11 along the tear seal, and the selvage portions 13 of both strips 12 and 14 are pulled back with the front cover 15. This separation of the sheath 11 and selvage 13 occurs because the tear seal tears down the middle of the seal line 21 leaving the upper and lower selvage portions welded together at the tear seal and the upper and lower portions of the sheath 11 welded together at the tear seal, thereby forming the sheath 11 as described in U.S. Pat. No. 3,809,230. Thus, as the front cover 15 is peeled back, the longer thermoplastic strip 12 is pulled back with the front cover strip 15, and the selvage of the longer thermoplastic strip 12 tears away from the tip portion 19 along the tear line. As the peeling continues, the selvage of the shorter thermoplastic strip 14, being welded to the selvage of the longer thermoplastic strip 12 along the outer portion of the tear seal, is pulled by the selvage of the longer thermoplastic strip 12 as the selvage of the strip 12 is pulled back with the front cover strip 15 and the selvage of the strip 14 and strip 12 together tears away from the sheath 11 along the seal line 21.

Figure 3B:
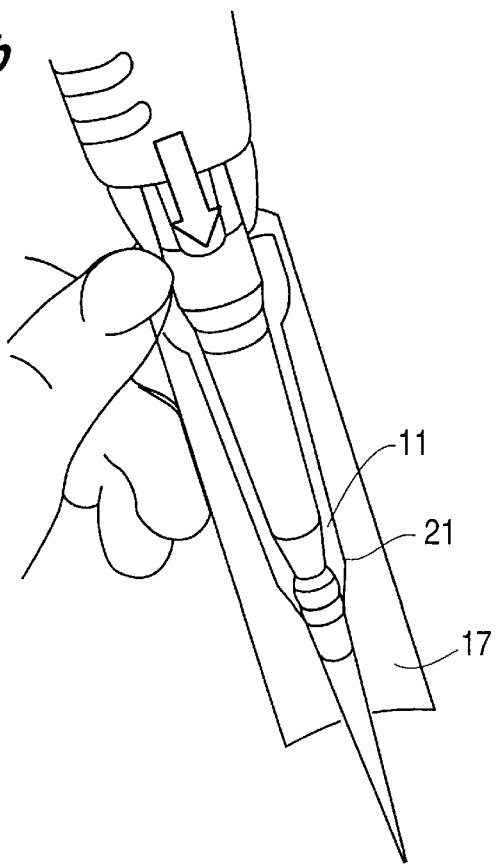
Figure 3C:
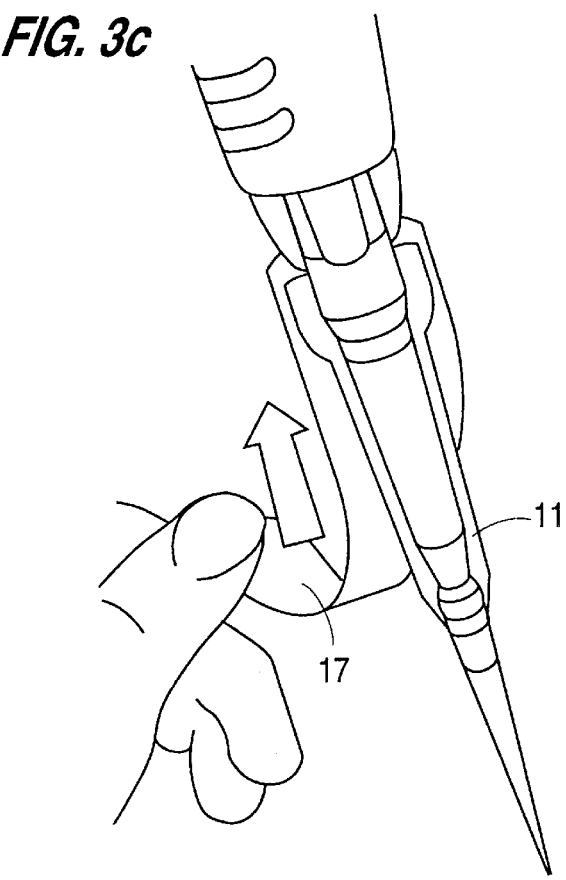
Figure 3D:
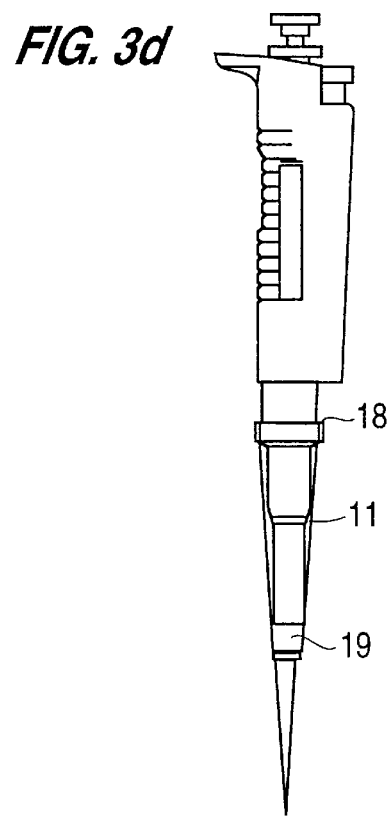

After the removal of the front cover 15, the pipetter is pushed down into the sheath 11 until the tip of the pipetter is pushed through the hole 16 formed by the die at point B as shown in FIG. 3b. FIG. 3c illustrates the subsequent removal of the back cover 17, leaving the sheath 11 on the pipetter as illustrated in FIG. 3d.

FIGS. 4a through 4e illustrate the use of the pipetter with the sheath 11 thereon. The pipetter and sheath 11 are placed into a test tube in a vertical orientation (FIG. 4a), and liquid is drawn out of the test tube and into the pipetter tip (FIG. 4b). FIGS. 4a and 4b further illustrate how the portion of the pipetter above the plastic tip enters the confines of the test tube, and how the sheath 11 protects the inner walls of the test tube and the liquid therein from contamination by the pipetter. The pipetter is then placed into the test tube which is to receive the liquid (FIG. 4c), and dispensed therein (FIG. 4d). FIG. 4e illustrates the pipetter tip and the sheath 11 being removed from the pipetter so that a new pipetter tip and sheath 11 may be placed thereon.

While the invention has been described in terms of the aforementioned embodiments, those skilled in the art will recognize that the invention can be practiced with modification within the spirit and scope of the appended claims.

We claim:

1. A packaging system for a pipetter sheath comprising:
   a front cover strip;
   a back cover strip;
   a first strip of thermoplastic material;
   a second strip of thermoplastic material, said first and second strip of thermoplastic material sandwiched between said front and back cover strips;
   a tear seal formed in said first and said second strips of thermoplastic material, wherein said tear seal forms a pipetter sheath comprised of said first and second thermoplastic strips, said pipetter sheath having a tip end and a mouth end;
   said first strip of thermoplastic material extending beyond said second strip of thermoplastic material;
   a tear line formed in the portion of said first strip of thermoplastic material extending beyond said second strip and connecting to the tear seal at the tip end of said sheath;
   a first peelable seal between said front cover strip and said first strip of thermoplastic material; and
   a second peelable seal between said back cover strip and said second strip of thermoplastic material.

2. A packaging system for a pipetter sheath according to claim 1, wherein said tear seal, said tear line, and said first and second peelable seals are formed by a U-shaped electromagnetic die.

3. A packaging system for a pipetter sheath according to claim 1, wherein the inside of said front and said back covers are coated with a thermoplastic material.

4. A packaging system for a pipetter sheath as recited in claim 1, wherein said tear line is U-shaped and extends between the ends of said tear seal at the tip end of said sheath.

5. A packaging system as recited in claim 1, wherein said first strip of thermoplastic material is joined to said front cover at the end of said front cover beyond the tip end of said sheath.

6. A method for placing a sheath onto a pipetter, said sheath being in a package as described in claim 1, comprising the steps of:
   grasping said front cover at said tip end of said package;
   pulling said front cover back to cause selvage of said first thermoplastic strip to separate from the portion of said first thermoplastic strip lying inside said tear line;
   placing a pipetter tip on a pipetter into said sheath at the mouth end of said sheath so that said sheath covers the upper portion of said pipetter tip and a portion of said pipetter directly above said pipetter tip;
   removing said front cover from said sheath;
   removing said back cover from said sheath thereby leaving said sheath on said pipetter; and
   using said pipetter to transfer a sample from one container to another.

* * * * *